(12) United States Patent
Rabiner et al.

(10) Patent No.: US 6,527,115 B2
(45) Date of Patent: Mar. 4, 2003

(54) DISPENSATION AND DISPOSAL CONTAINER FOR MEDICAL DEVICES

(75) Inventors: Robert A. Rabiner, North Reading, MA (US); Bradley A. Hare, Chelmsford, MA (US); James H. Loper, Wales, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 10 days.

(21) Appl. No.: 09/775,908

(22) Filed: Feb. 2, 2001

(65) Prior Publication Data

US 2002/0117412 A1 Aug. 29, 2002

(51) Int. Cl.$^7$ .............................................. B65D 83/10
(52) U.S. Cl. .............................. 206/363; 206/438; 220/8
(58) Field of Search ................................ 206/363, 364, 206/365, 366, 438; 220/8; 345.1, 345.2, 345.3, 345.4, 908; 215/322

(56) References Cited

U.S. PATENT DOCUMENTS

| | | | |
|---|---|---|---|
| 3,967,621 A | * | 7/1976 | Schwarz ..................... 604/192 |
| 4,479,585 A | | 10/1984 | Sandhaus |
| 4,862,573 A | * | 9/1989 | Kelson et al. .............. 206/366 |
| 5,129,914 A | | 7/1992 | Choi |
| 5,323,902 A | * | 6/1994 | Palmer et al. .............. 206/366 |
| RE36,693 E | * | 5/2000 | Reich ....................... 250/507.1 |
| 6,062,001 A | * | 5/2000 | Kunik ........................ 206/366 |

OTHER PUBLICATIONS

PCT International Search Report for International Application No. PCT/US02/01885 dated Jun. 11, 2002.

* cited by examiner

Primary Examiner—Shian Luong
(74) Attorney, Agent, or Firm—Palmer & Dodge, LLP; Richard B. Smith (57) ABSTRACT

The invention is directed to a container for storage, dispensation, transport and disposal of a medical device such a disposable ultrasonic surgical probe, that allows its dispensation for use, and for its safe storage and disposal after use, thereby protecting the user from the hazards of needle pricks and possible contamination from small-diameter probes. The container of the present invention also provides a mechanism for restricting access to the probe to prevent its reuse, and a method for its safe attachment to and detachment from an ultrasonic medical device. The container comprises a cylindrical tube having two ends and an inner surface defining a space for containing the probe. The probe is held within the cylindrical section of the container by a locking means that allows a single dispensation for its use and enables its disposal after use in an inaccessible manner, so as to enable its attachment and detachment to the non-disposable segment of the device such as an ultrasonic probe handle without requiring direct handling by the user. The user, is therefore protected from against accidental sticks from a possibly contaminated probe. The container also prevents re-use of the probe, and provides a means for its safe disposal.

22 Claims, 5 Drawing Sheets

DISPENSATION AND DISPOSAL CONTAINER FOR MEDICAL DEVICES

FIELD OF THE INVENTION

The present invention relates generally to a container for storage, dispensation, transport and disposal of a medical device. More particularly, this invention is directed to a container for storing a sterile ultrasonic surgical probe that allows its dispensation for use, and for its safe storage and disposal after use, thereby protecting the user from the hazards of accidental needle sticks and possible contamination from small-diameter probes. The container of the present invention also provides a mechanism for restricting access to the probe to prevent its reuse, and a method for its safe attachment to and detachment from an ultrasonic medical device.

BACKGROUND OF THE INVENTION

The increased utilization of disposable medical devices such as scalpels, syringes, lances needles, and the like, commonly referred to as "sharps" is raising concern with regard to the safe disposal of such devices. Improper handling of sharps by medical and healthcare personnel is attributed to being the leading cause of accidental skin puncture wounds. The consequences of such injuries can be life threatening, since used medical devices that are contaminated with blood and other biological media can result in transmission of dangerous infectious diseases such as hepatitis and AIDS. Furthermore, conventional disposal units for such devices do not normally allow for positive neutralization of the biological hazard at the site of the surgical procedure. Such devices, therefore, may contain contaminating bacterial and viral species that remain viable as the device is transported from the site through a waste hauling system to a decontamination facility. Additionally, a number of currently used disposal devices, especially sharps, do not affirmatively lock when closed, resulting in their being accidentally or intentionally reopened thereby exposing medical and waste disposal personnel to potentially dangerous biological contaminants.

Various devices have been proposed in the art for disposal of sharps. Sharps containers in the art typically include a valved opening, and a closure mechanism (see, e.g., model 5400 series available from Becton Dickinson and Company of Rutherford, N.J.) or non-valved openings (see, e.g., U.S. Pat. No. 4,569,554). The containers typically can be filled with multiple sharp objects. Other sharps containers (Model 8600, Becton Dickinson and Company of Rutherford, N.J.) include a mechanism to disable a sharp object being disposed of (e.g., a needle), but also invites filling with multiple sharp objects. A great majority of sharp containers disclosed in the art (for example in U.S. Pat. Nos. 4,666,538, 4,804,090, 4,842,138 and 5,281,391, 5,630,506) are limited to the disposal of needles, more particularly syringe needles, and are designed to be disposal containers capable of accepting and containing several units, after which the container is sealed and transported for disposal. Since these containers are designed for disposal only, they offer only a limited advantage, since they do not obviate the need for the healthcare professional to manipulate the needle manually to detach it from the syringe prior to discarding them in such containers. The aforementioned risks of accidental injury are, therefore, not precluded.

While many of the prior art devices have provided innovative and improved disposal methods for sharps, more particularly, needles, these devices suffer from some of the following disadvantages:

i) inadequate design for disposal of single use specialty devices such as probes, catheters, guide-wires and other non-permanent implants. Although such devices that have to be disposed of taking the same precautionary steps as needles to prevent accidental contamination, they are presently discarded using conventional disposal devices that require physical handling by the healthcare personnel.

ii) they require direct handling of sharps by medical personnel to remove them from manufacturers sterile packaging for attachment to ancillary devices such as a handle of a surgical device or a dispensing syringe, and for their subsequent detachment from said ancillary device for discarding into a disposal container. Such handling can result in inadvertent microbiological contamination of the sharp prior to use that can pose risk of infecting the patient, and pose concerns of health hazard to the healthcare provider arising from contact with contaminated biological materials such as blood or tissue from the used device during the process of detaching them from the ancillary device for their disposal.

iii) they do not offer efficient means to remove new sharps from sterile packaging, their attachment and detachment to device ancillary units, and disposal without substantial human contact, thereby eliminating inadvertent injury caused by handling the sharps and associated concerns such as contaminating unused sharps prior to use on a patient, or contracting contagious diseases from used contaminated sharps.

Due to the recent advent of disposable forms of devices such as endoscopes, ultrasonic tissue ablation probes, and the like, previously only being envisioned as reusable devices, there exists a significant need for an improved apparatus for containing devices (herein referred to as "container") and methods for dispensation, storage and safe disposal of such devices, that allows their easy removal for use substantially without direct human contact, and subsequent placement of the device in the same container after its use again without requiring such direct contact. It is also desirable for the container to maintain used devices contained in them such that they are substantially isolated from further access during handling for disposal. There is also a need for the container to be able to preclude retrieval of used medical devices placed in them, thereby discouraging their unauthorized reuse. Additionally, it is desirable to have the ability to package new unused medical devices such as "sharps" in the multi-functional container that enables dispensation, storage and disposal of the device. Presently, new sharps are typically packaged and transported in one type of container and disposed in another container after use. Furthermore, it is generally recognized by those skilled in transport and delivery of medical instruments and devices that it is critically important to provide evidence of tampering for each user immediately prior to opening a container of new medical instruments and devices.

Ultrasonic surgical probes, especially those operating in transverse mode described in applicants co-pending provisional applications U.S. Ser. Nos. 60/178,901 and 60/225,060, have a plurality of regions of maximum energy referred to as nodes, along the length of the probe. This results in a plurality of regions of high stress, resulting in potential for degradation of structural integrity of the probe. Repetitive use of the probe can potentially worsen this problem, with inadequate means by the user to determine the residual life of the probe. Stress fractures may develop, creating a greater tendency for the probe to shatter with the potential of foreign bodies being induced into the patient, or resulting in microscopic irregularities in the surface that may render the probe difficult to decontaminate between uses. As such, ultrasonic probes should be treated as single use, single patient contact medical devices, and after each use be considered medical waste. Where a probe sheath is also used in conjunction with the probe, the small sheath lumen will incorporate blood and cellular debris during use, which due to their small diameter, render them extremely difficult to clean. For safety purposes they should be discarded.

Medical waste disposal devices also do not normally allow visual inspection and counting of enclosed sharps or other devices after the devices is closed, thereby precluding an accounting means to ensure the number and type of medical waste included in such sealed containers. Furthermore current medical-waste disposal methods typically require large treatment systems involving complex operation that are non-portable and highly expensive. Such systems include autoclaving, incineration and bulk chemical treatment of the medical device waste. It is therefore, desirable to provide an improved portable disinfecting and disposal device for such medical device waste.

Based on the aforementioned limitations in the current disposal containers for medical devices disclosed in the art, and a lack of an efficient container that functions both as a dispensing as well as a disposal container for a disposable surgical device in the art. There is a need for such a dispensing and disposal container for sharp disposable medical devices, such as a small diameter ultrasonic probe used for tissue ablation. Such probes are described in the Applicant's co-pending provisional applications U.S. Serial Nos. 60/178,901, and 60/225,060 which further describe the design parameters for an ultrasonic probe operating in a transverse mode and the use of such a probe to remodel tissues, as well as the Applicants co-pending utility application Ser. No. 09/776,025 entitled "Ultrasonic medical device operating in a transverse mode for removing occlusions" which describes the use of such probes combined with probe sheath assemblies that modulate the cavitation energy emitted by the probe, and catheter balloon assemblies for removing blood vessel occlusions. The entirety of these applications are herein incorporated by reference.

SUMMARY OF INVENTION

It is therefore an object of the present invention to provide a tamper-resistant light-weight container for safely holding a medical-surgical device, allowing its dispensation of the device from the container for use, and for it's disposal after use, without requiring direct touching or handling of the probe itself. The device containment segment of the container may be rigid, or flexible with rigid ends to accommodate devices that are flexible.

It is yet another object of the present invention to provide such a container to hold, dispense and dispose of medical sharps safely, particularly thin ultrasonic probes utilized for tissue ablation and removal of occlusion materials from vascular occlusions in blood vessels.

It is yet a further object of the invention to provide a container for an ultrasonic probe that is capable of dispensing a new probe or probe assembly for attachment to an ultrasonic surgical device, and for detaching the probe from the said device, without requiring direct handling of the probe or probe assembly.

It is another object of the present invention to provide a container for a medical device such as an ultrasonic probe, consisting of a tamper resistant locking mechanism that prevents reuse of a used device disposed within by precluding access to said device.

It is yet another object of the invention to provide a container for a medical device such as an ultrasonic probe which may be disposed of simultaneously with the disposal of the used medical-surgical device, thereby obviating the need for sterilizing the container itself.

Briefly summarized, the foregoing objects are achieved by a container assembly which is utilized for both storing and dispensing new sharps such as a small diameter ultrasonic probes and accompanying accessories, if any, such as sheath assemblies, balloon catheters, etc. prior to use, and receiving such contaminated or used devices for storage, transport and disposal.

The preferred embodiment comprises a container for an ultrasonic probe which prevents the probe's reuse and provides a method for dispensing and disposing an ultrasonic probe. The container is designed for containing a probe or probe assembly, a means for attaching the probe to an ultrasonic medical device, a means for simultaneously containing the used probe while detaching the probe from the ultrasonic medical device, without requiring direct handling of the probe.

The container comprises a hollow cylindrical tube having two collar assemblies (herein referred to as "Collar") at the open ends that function as lids. The inner diameter and length of the cylinder with an inner dimension defining a space for the probe and its accompanying accessories, if any. The collars are designed to be adaptable to cylinders with varied lengths and diameters to accommodate probes and probe assemblies of different dimensions. Each collar comprises of two segments, both of which have apertures centrally located, having diameters that correspond to the dimension of the probe or probe assembly for which the container is adapted. The said apertures in the collars permit access to the cylindrical segment of the container. The collars are also designed such that they are securely affixed to the container body in a manner that provides evidence of tampering when removed. A complement of tamper resistant mechanisms, including locking assemblies in the collars, are provided that render opening of the container relatively restricted. The locking mechanism within the collars are configured to function in a manner complementary with respect to each other, thereby enabling the collar at the dispensing end to permit a one-time dispensation of a new, unused device, whereas the collar at the disposal end permits receipt of used or contaminated device. The said locking mechanisms in the collar assemblies prevent the reuse of the container by substantially preventing the removal or re-dispensation of a previously disposed device in the associated container. The collar at the disposal end includes an area for placement of a used or contaminated device, wherein a person may then deposit the article into the container body without directly touching the device being disposed of. Additionally, the collar assembly prevents further handling of the used devices by medical personnel subsequent to disposal.

In a preferred embodiment, the collar assemblies have a larger diameter than the cylindrical tube section of the container. The interior surface of the collar assemblies are arcuate or conical shaped, tapering from a larger diameter at the end distal to the cylindrical section to a smaller diameter approaching the aperture, thereby providing a means of guiding or directing the used probe into the device, and also providing clearance for attaching or detaching the probe to or from the transducer. In another embodiment of the invention, an extended rigid or semi-rigid structure located around the collar provides a means of shielding the hand of the operator that holds the container while the probe is inserted.

Between the first and second segments of the collar is a locking mechanism capable of manipulation by the user. The first locking mechanism can be, for example a plate that slides along a groove in a direction perpendicular to the longitudinal axis of the container. Alternatively the locking mechanism can be a rod or an extrusion. The locking means is adapted for engaging the medical article or device stored or disposed within the container. In a preferred embodiment, the locking mechanism is capable of engaging the proximal end an ultrasonic probe at one or more grooves or threads located at proximal end of said probe or at a depression, aperture, or a raised surface designed on the probe at its proximal end. At one end of the container (herein referred to as "dispensing end"), articulation of the locking means by the operator, disengages the locking mechanism from the probe, thereby allowing its release from within the container for dispensation. At the end opposite from the dispensing end of the container (herein referred to as "disposal end"), articulation of the locking mechanism by the operator engages the probe thereby securing the probe irreversibly within the container, thereby preventing further access. The locking mechanisms are capable of securing the probe immovably within the container, thereby providing a mechanism for communicating torsional forces applied to the probe, for example, when the probe is affixed to or detached from an ultrasonic medical device. The attachment the probe and its detachment from the medical device can be accomplished for example, by screwing the probe on to, or off of the device, by rotating the device handle after affixing it to the proximal end of the probe. In other embodiments of the invention the locking mechanism can be threaded, or a ratcheting means, or other such ways of constraining the probe in a unidirectional manner while torsional forces are applied to the container to effectuate attachment or detachment of the probe from the ultrasonic medical device.

In another embodiment, the container of the invention comprises a single open end having a plurality of locking assemblies, thereby enabling the dispensation and disposal of a medical device from the same end of said container. In a further embodiment, the container of the invention comprises of a single open end having a single locking assembly, thereby enabling its utilization exclusively for safe disposal of used medical devices and articles.

In one aspect, the container of the present invention is provided together with an ultrasonic probe contained therein in the form of a kit. In another aspect, container of the present invention is provided together with a probe comprising accessories such as a sheath assembly, balloon catheter, and the like contained therein, as required for specific surgical procedures. In yet another aspect of the invention, the container within the kit with the probe and accessories, if any contained therein, further comprises packaging, whereby said container and its contents are pre-sterilized, and sealed against environmental contaminants. In another aspect, the container comprising the probe and accessories are provided in a manner complying with regulations governing packaging, storage, handling, transport and disposal of sharp medical devices.

In a preferred embodiment, the container provides a means of attaching the ultrasonic probe together with its accessories to an ultrasonic medical device, and further provides a means for detaching them from the said device, without necessitating direct manipulation or handling of the probe (and its accessories if any), and a means for removing the said probe and assembly from the ultrasonic medical device after use. In one aspect, container having a probe contained within provided a sterile kit, comprises single use locking mechanisms located at the dispensing and disposal ends of said container, wherein said locking mechanism at the dispensing end enables attachment of the probe to an ultrasonic medical device solely through the said container, thereby allowing its dispensation from within the container, and wherein the said locking mechanism at the disposal end allows its disposal into the container in a manner preventing re-insertion of the probe through the dispensing end and re-extracting the used probe from the disposal end.

The foregoing specific objects and advantages of the invention are illustrative of those that can be achieved by the present invention, and are not intended to be exhaustive of the possible advantages that can be realized. Thus these, and other objects and advantages of the invention will be apparent from the specifications and drawings, herein or can be learned by practicing the invention, both as embodied herein or as modified in the view of any variations which may be apparent to those skilled in the art. Accordingly, the present invention resides in the novel parts, construction, configurations, improvements and utility herein shown and described.

BRIEF DESCRIPTION OF THE DRAWINGS

FIG. 6 shows a sectional view the locking mechanisms within the collar at the disposal end (6a and 6b).

FIG. 7 shows a sectional view the locking mechanisms within the collar at the dispensing end (7a and 7b).

DETAILED DESCRIPTION OF THE INVENTION

"Container" as used herein refers to an apparatus used for safe dispensation, storage and disposal of a medical article or device, in most particularly, sharp medical devices.

Throughout this description, the terms "distal" and "proximal" when pertaining to description of a probe or probe assembly are relative to the operator, i.e. distal is away from the operator and indicates the forward end of the device, whereas proximal is nearest to the operator and relates to the rear end of the device.

When aforementioned terms are used pertaining to description of collar assemblies of the container, they are relative to the hollow cylindrical portion of the container wherein a medical device such as an ultrasonic probe is stored, i.e. "distal" is the segment of the collar that is furthest from the cylindrical section, whereas "proximal" refers to the segment that nearest to said cylindrical section.

"Dispensing end" and "Disposal end" as used herein refers to the ends of the container that allow dispensation and disposal respectively of a medical article or medical device.

"Probe" as used herein refers to a device capable of being adapted to an ultrasonic generator means, which is capable of propagating the energy emitted by the ultrasonic generator means along its length, and is capable of acoustic impedance resulting in transformation of ultrasonic energy into mechanical energy.

"Sharps" as used herein refers to an elongated medical instrument or medical device with a small diameter, for example, less than 2 mm. A "Sharps Container" as used herein is a container capable of retaining a sharp medical device or the sharp portion thereof, such that a handler is not exposed to the sharp portion of the device.

"Sheath assembly" as used herein refers to a device for covering, encasing, or shielding in whole or in part, a probe or portion thereof connected to an ultrasonic generation means.

In the drawings, like reference characters generally refer to the same parts throughout the different views. Also, the drawings are not necessarily to scale, emphasis instead generally being placed upon illustrating the principles of the invention.

Figure 1:
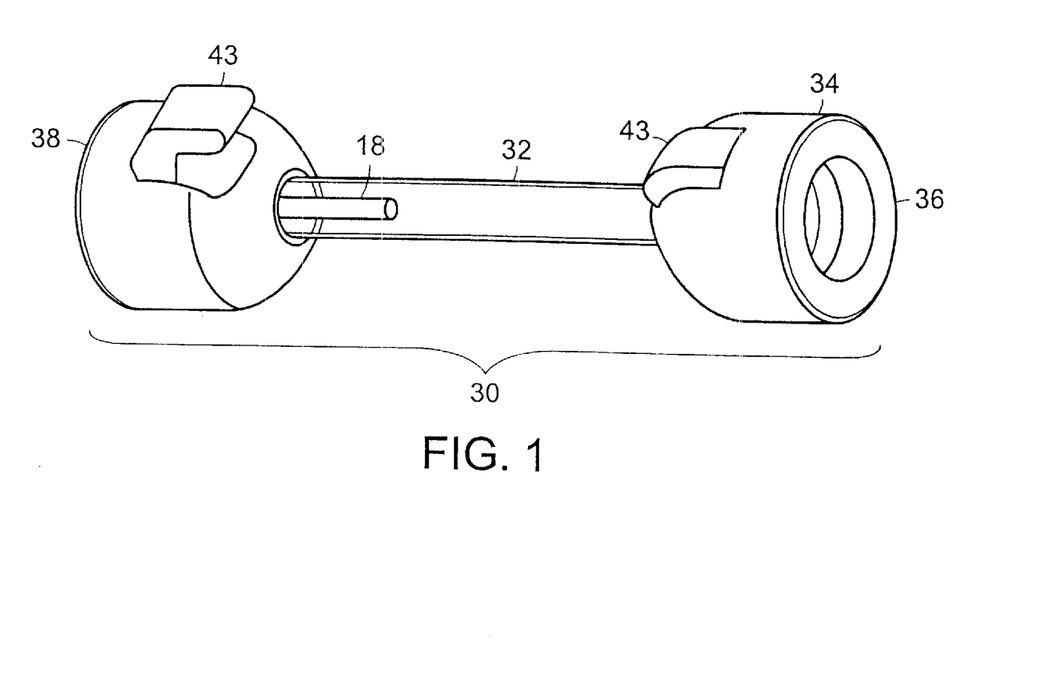
FIG. 1 shows the container for single use medical articles comprising a dispensing end and a disposal end.

FIG. 1 shows a "sharps" container 30 of the present invention for dispensing and disposal of an ultrasonic probe. Container 30 comprises a cylindrical section 32 capable of accommodating probe 18 (shown partially) terminally connected to collars 36 and 38 that form the dispensing and disposal ends respectively of container 30. Articulation levers 43 enable engagement of the locking mechanisms (not shown) within collars.

Figure 2:
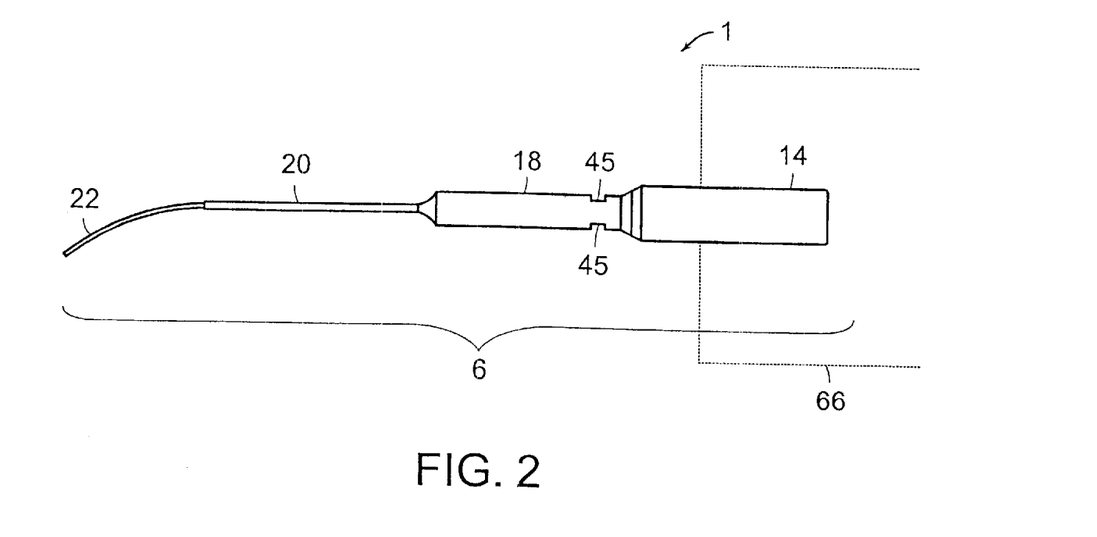
FIG. 2 shows a medical device comprising a disposable ultrasonic probe that is dispensed from and disposed into the container.

FIG. 2 shows a transverse mode ultrasonic medical device 1 comprising a disposable elongated probe 6 designed for a one time use, which is coupled to a device handle 66 that contains a source or generation means for the production of ultrasonic energy (shown in phantom in the figure as 66) that is transmitted to said probe to enable its function. In the example shown, the probe diameter decreases at defined intervals 14, 18, 20, and 22. In this example, probe interval 18 has at least one groove 45 at the end proximal to probe handle 66. Groove 45 is capable of being engaged by the locking mechanisms at the dispensing and disposal ends of the container 30, so as to constrain the probe within the cylindrical volume of said container, thereby enabling its dispensation and disposal without requiring direct handling of the probe itself.

Figure 3:
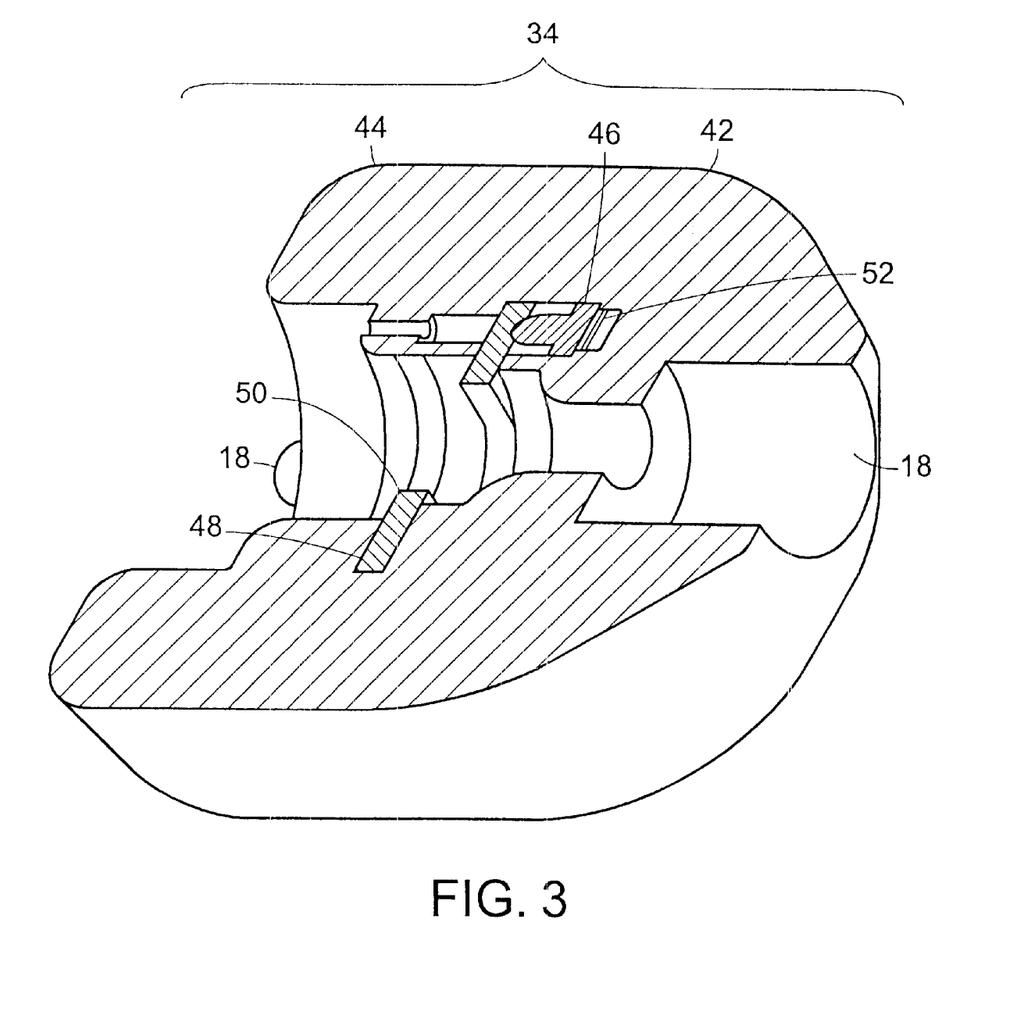
FIG. 3 shows the ultrasonic probe of the surgical device inserted into the container for disposal.

FIG. 3 shows a cross-sectional view of collar 34 comprising of two segments, a first segment 42 proximal to the cylindrical section (not shown) and a second segment 44 distal to the tube. Between the first and second segments is a locking mechanism capable of being engaged by the user. In one embodiment, the locking means can be engaged by a lever, not shown in this view. The lever extends laterally to the outside of the collar assembly, allowing articulation by the user. The lever engages the locking mechanism, causing it to slide laterally within a groove in segment 42 of the collar. In a preferred embodiment, the locking mechanism comprises a locking assembly, such as for example, a plate 48 having a keyhole shaped slot 50, both shown partially, and a pin-hole (not shown) capable of sliding over a pin 46 seated on a spring 52 that exerts a unidirectional force on the pin. Upon engaging the locking mechanism, for example with a lever, plate 48 is capable of sliding over pin 46 so as to align pin-hole in the plate with the pin, thereby rendering it capable of receiving the pin. The pin is forced into the pinhole by spring so as to "lock" the plate, rendering it incapable of further lateral movement since it is constrained within the collar assembly. The locking assembly, once engaged by the pin, is therefore prevented from retrograde articulation. The keyhole shaped slot 50 in the plates at the dispensing and disposal ends of the container are aligned inversely with respect to one another, so as to permit dispensation and disposal of the probe respectively, upon activation of the locking mechanisms at the respective ends, by engaging or disengaging groove 45 in the probe.

Figure 4:
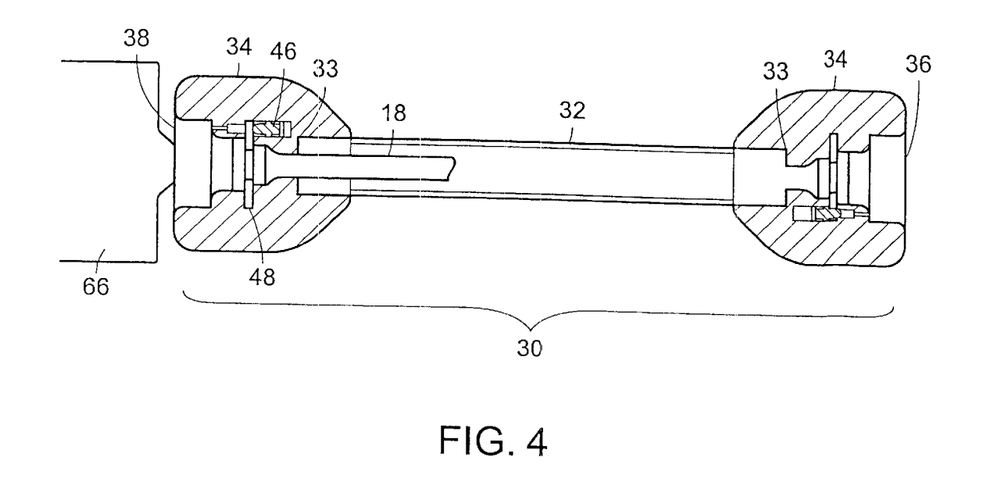
FIG. 4 shows cross-sectional view of the collar assembly comprising the locking mechanisms enabling, irreversible dispensation and disposal respectively of a medical article.

FIG. 4 shows, a used ultrasonic probe 18 (shown partially) that is still connected to probe handle 66 inserted into the disposal end of the container through collar 38 prior to its disposal within cylindrical section 32. Disposal of the probe is accomplished by depressing lever (not shown) that articulates locking assembly 48 within the collar assembly 34, causing said locking assembly to move to a irreversibly to a "locked" position wherein pin 46 is aligned with a slot in the locking assembly 48, further causing pin 46 to be forced into the slot by the unidirectional force exerted by a spring (not shown) on said pin. The locking action of assembly 48 engages a groove or set of grooves (not shown) in probe 18 located at the end proximal to probe handle 66, thereby causing said probe to be restrained irreversibly within container 31. The probe is subsequently disengaged from the handle 66 by turning the latter in a counter clockwise direction, thereby releasing the probe into container for safe disposal.

Figure 5:
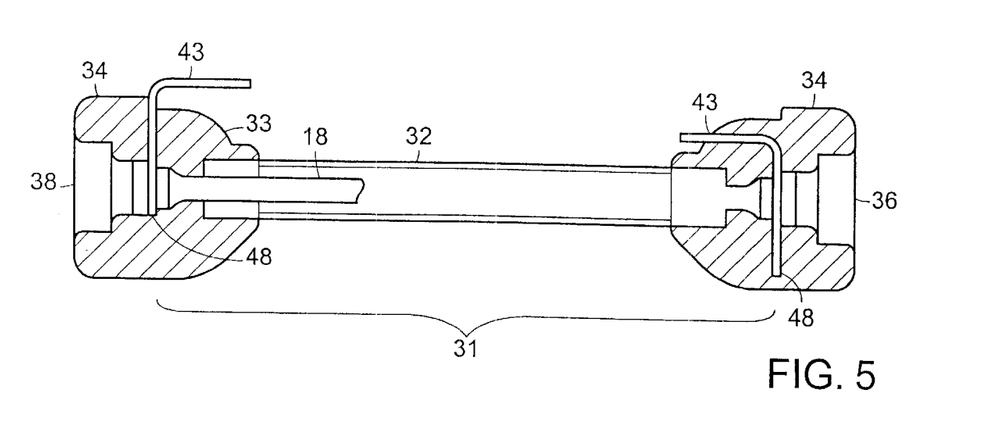
FIG. 5 depicts the container with a cross-sectional view of the collar assemblies at the dispensation and disposal ends showing the articulation handles for engaging the locking mechanism within the collars.

FIG. 5 shows container 31 and a cross-sectional view of collars 34 illustrating the locking assembly plates 48 connected to articulation handles 43 at disposal end 36 and dispensing end 38 of the container. The locking mechanism of container 31 at disposal end 36 is adapted to engage probe 18 in a specific manner to enable its disposal as shown, such as for example, by engaging one or more set of grooves in the probe proximal to the probe handle 66. Engaging the locking mechanism by depressing lever 43, causes plate 48 to slide laterally within the space defined by collar assembly over pin (not shown in this view), forcing the pin to align with and engage a pinhole in plate 48, thereby "locking" the plate. Rendering the plate "locked" further causes said locking mechanism to engage probe 18 in an irreversible manner, thereby preventing its re-dispensation. Upon disengagement of the probe from device handle (not shown in figure), the probe is deposited within container for disposal. The irreversible engagement of the locking mechanism, therefore, prevents access to the probe disposed within the container.

Figure 6A:
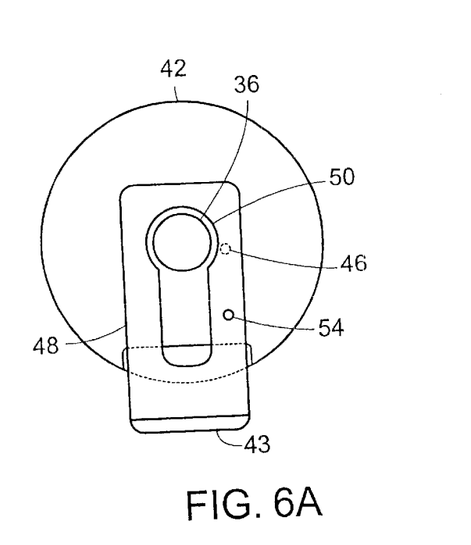
Figure 6B:
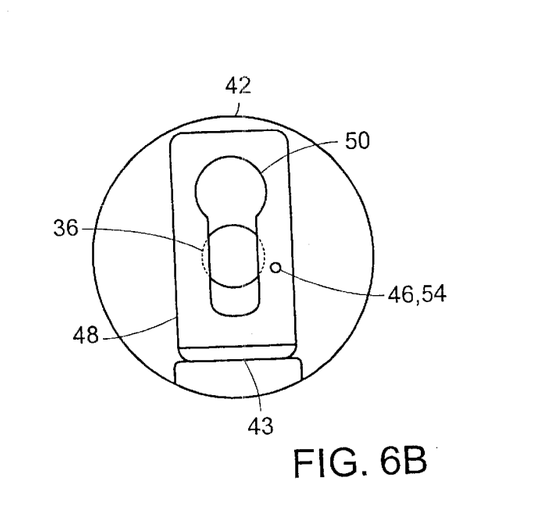

FIG. 6 shows sectional views of collar segment 42 at the disposal end 36 comprising of a central aperture 36 capable of communicating with the cylindrical section of container (not shown in this view). A locking assembly comprising plate 48 having a key hole shaped slot 50 is capable of being articulated by lever 43, thereby causing it to slide laterally over aperture 36. Plate 48 further comprises pinhole 54 capable of aligning with pin 46 seated on a spring (not shown in this view) within collar segment 42 such that it exerts a unidirectional force on pin 46, thereby causing the pin to remain in intimate contact with plate 48. When locking mechanism is in the non-locked position (FIG. 6a), the circular section of the key hole slot 50 in plate 48 is aligned with aperture 36, thereby enabling insertion of a used probe for disposal. Articulation of the locking mechanism by depressing lever 43 causes plate 48 to slide laterally over aperture 36, thereby causing the circular segment of keyhole shaped slot 50 to be displaced from aperture 36. The lateral movement of plate 48 further causes pinhole 54 to aligned with pin 46 such that pin 46 irreversibly enters pinhole 54 by action of the spring, thereby causing plate 48 to remain in the "locked" position, wherein the rectangular segment of keyhole slot 50 engages a groove or set of grooves on the probe at the end proximal to the device handle. The irreversible action of the locking mechanism, therefore, precludes subsequent retraction of the probe after its disposal into the container and activation said locking mechanism.

Figure 7A:
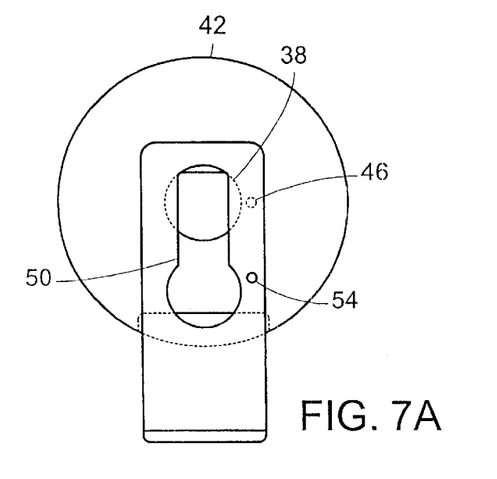
Figure 7B:
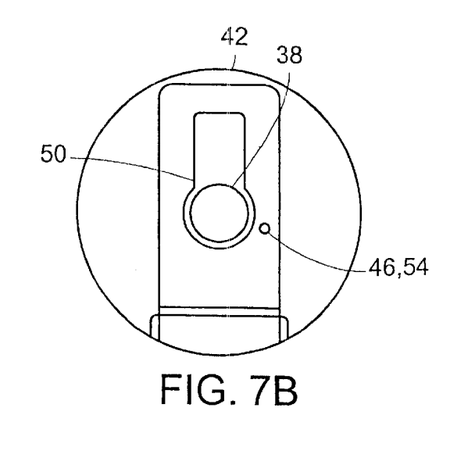

FIG. 7 shows sectional views of collar segment 42 at the dispensing end. The arrangement of components and articulation of the locking mechanism is identical to that at the disposal end illustrated in FIG. 6 as described in the foregoing section, with the exception of the orientation of key hole slot 50, which is inverse to that at the disposal end (FIG. 6). The inverse orientation of slot 50 causes an unused probe to be restrained in a non-retractable manner when the plate 48 of locking mechanism is in a non-locked position (FIG. 6*a*), and allows retraction of the said probe for dispensation upon moving plate 48 to a locked position by articulation of lever 43. Dispensation of the probe is accomplished by attachment of the probe handle of a medical device to the proximal end of the probe, following which engaging the locking assembly by articulation of lever 43 to cause plate 48 to move irreversibly into a "locked" position further causes alignment of aperture 38 with the circular segment of keyhole 50, thereby enabling retraction of probe from the container. The irreversible movement of plate 48 in a locked position precludes re-insertion of probe into container for re-dispensation.

Dispensation and disposal of an ultrasonic probe using the container of the invention is accomplished in the following manner. A new unused probe packaged in the container with the locking mechanism at the dispensation in the non-locked position so as to constrain the probe within said container is, dispensed by inserting probe handle into collar at dispensing end, affixing probe to the handle by clockwise rotation causing threads on the probe handle to engage complementary threads in the device handle, depressing the lever at that end results in articulation of the locking mechanism 48 thereby disengaging the said locking mechanism from the grooves on the probe and allowing the operator to withdraw the probe from the container. After the probe has been used and is ready for disposal, the operator inserts the probe at the disposal end of the container. Engaging the locking mechanism at the disposal end causes the used probe to be secured within the container, thereby enabling detachment of the probe handle by counter clockwise rotation to disengage the threads on the probe from the complementary threads on the handle. The used probe is permanently engaged by and contained within the container, and can be disposed of in compliance with the provisions governing the disposal of medical waste. Because the probe assembly is contained by the invention, the sharp probe tip does not present a safety hazard, and can be safely handled and disposed of as medical trash.

Materials useful for the present invention include any material rigid or semi-rigid materials that are substantially resistant to puncture from a sharp medical instrument, and capable of being sterilized by, for example, gamma irradiation or ethylene oxide gas (ETO), without losing their structural integrity. Such materials include but are not limited to, rubber, or plastics such as polytetrafluoroethylene (PTFE), polyethylene, polypropylene, silicone, polyetherimide or other similar plastics. Ceramic, metallic, and glassy materials can also be used, and have the added benefit being sterilizable by autoclaving. Where sterilization by ultraviolet irradiation is contemplated the materials for construction of the container must be substantially UV-transmissible. Combinations of the aforementioned materials can be used. The proportions of the device depend on the probe that will be contained within the device. A container that is designed to accommodate a probe of for example, eight inches long, would utilize a tube approximately the same length. The diameter of the tube must be sufficient to accommodate the probe, which will vary depending on the shape of the probe tip, for example, straight, rounded, curved, crescent, or "U" shaped, or the presence of a probe sheath. Glass or clear high-density plastic is preferred as the probe itself can be visualized in the container. The collar assembly has an inside diameter at least as wide as the tube, with an outside diameter greater than the inside diameter. In the preferred embodiment, the outside diameter of the collar is at least two to five times the inside diameter, and the inside surface tapers in width from the widest point at the terminus of the collar, and narrows proximally to the cylindrical section of the container. This taper provides a means to guide the probe into the tube, and it also provides clearance between the inside surface of the collar, allowing attachment to the ultrasonic medical device. A large outer diameter for the collar provides greater shielding capability to protect the hand of the operator from accidental pricks when a used probe is inserted into the container. The collar assembly may be manufactured out of any substantially rigid material that will not deform, crack, or shatter under the torsional forces generated from attaching or detaching the probe to the ultrasonic medical device, for example, high density plastic, metal, ceramic, or hard rubber, and the like.

It should be obvious to those of ordinary skill in the art that the individual features described herein may be combined. Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

We claim:

1. A container for dispensation, storage, transportation and disposal of a medical device comprising:

a hollow cylindrical section comprising at least one open end comprising a closure assembly adapted to said open end, including means for mounting thereto, comprising an access opening adapted to dispense, receive and retain the medical device;

an access controlling means adapted to said closure assembly interacting with the container and said access opening;

said access control means comprising of at least one locking mechanism formed integrally with said closure assembly and movable under the action of an actuating means from a non-locked position to a locked position wherein said locking mechanism engages the medical device;

said actuation means further comprising an articulation apparatus whereby application of pressure on said apparatus results in movement of said locking mechanism from a non-locked to a locked position, and means for positively retaining said locking mechanism in said locked position after movement thereto from said non-locked position.

2. The container of claim 1 wherein the closure assembly comprises a collar having at least two non-detachable segments, a first segment proximal to the cylindrical section of said container and a second segment distal to the said cylindrical section, said segments have access openings that communicate with the cylindrical section of said container, further having said locking mechanism disposed between said segments, and said articulation apparatus to activate said locking mechanism.

3. The container of claim 2 wherein the locking mechanism comprises a rectangular plate having a slot capable of moving over a pin attached to the collar segment proximal to the cylindrical section, said pin seated on a spring, said spring engaged to the first segment of the collar and said spring being capable of exerting a unidirectional force enabling said pin to make intimate contact with said plate, whereby movement of the said plate causes said pin to be forced into the slot in causing said mechanism to lock in an irreversible manner.

4. The container of claim 2 wherein the locking mechanism is attached to said articulation means extending externally from the collar, capable of moving said locking mechanism from a non-locked position to a locked position.

5. The container of claim 2 wherein the collar has an inside diameter that is greater than the inside diameter of said tube.

6. The container of claim 2 wherein the inner diameter collar is large at a terminal end of said container, and tapers to a smaller diameter approaching the access opening proximal to the cylindrical section of said container.

7. The container of claim 2 wherein the collar comprises an additional extended structural assembly positioned around said collar to provide a means of shielding the hand of a user from the medical device during its dispensation from or disposal into said container.

8. The container of claim 1 containing at least two locking mechanisms, a first locking mechanism capable of engaging the medical device in the locked position and disengaging from said probe in the unlocked position upon activation, and a second locking mechanism capable of engaging an ultrasonic probe in the unlocked position and disengaging from said medical device in the locked position upon activation.

9. The container of claim 1 comprising a single open end for disposal of the medical device.

10. A container for dispensation, storage, transportation or disposal of a medical device comprising:
 a cylindrical section having a first open end and a second open end;
 a first collar assembly engaging the first open end and a second collar assembly engaging the second open end wherein each of the first collar assembly and the second collar assembly further comprise an access opening adapted to dispense and receive the medical device;
 a first locking mechanism engaging the first collar assembly and a second locking mechanism engaging the second collar assembly wherein the first locking mechanism and the second locking mechanism are capable of moving between a first unlocked position and a second locked position; and
 an actuator capable of controlling the movement of the locking mechanism between the first unlocked position and the second locked position wherein the actuator extends externally from the collar assembly,
 wherein the first locking mechanism is capable of engaging the medical device in the first unlocked position and disengaging from the medical device in the second locked position upon activation and the second locking mechanism capable of engaging the medical device in the second locked position and disengaging from the medical device in the first unlocked position upon activation; and
 wherein the first locking mechanism and the second locking mechanism each comprise a rectangular plate having a slot capable of moving over a pin attached to the first non-detachable segment proximal to the cylindrical section of the container, engaging a spring, the spring engaging the first non-detachable segment proximal to the cylindrical section and the spring capable of exerting a force enabling the pin to engage the rectangular plate, whereby movement of the rectangular plate causes the pin to be forced into the slot and causes the locking mechanism to lock.

11. The container of claim 10 wherein the cylindrical section is hollow.

12. The container of claim 10 wherein the first collar assembly and the second collar assembly each comprise a first non-detachable segment proximal to the cylindrical section of the container and a second non-detachable segment distal to the cylindrical section of the container wherein the first non-detachable segment and the second non-detachable segment each have an access opening in communication with the cylindrical section of the container.

13. The container of claim 11 wherein the first locking mechanism is located between the first non-detachable segment proximal to the cylindrical section of the container and the second non-detachable segment distal to the cylindrical section of the container of the first collar assembly.

14. The container of claim 10 wherein the collar assembly has an inside diameter that is greater than an inside diameter of the cylindrical section.

15. The container of claim 10 wherein the collar assembly comprises a first inside diameter at a first end of the collar assembly proximal to the cylindrical section and a second inside diameter at a second end of the collar assembly distal to the cylindrical section wherein the first inside diameter is smaller than the second inside diameter.

16. The container of claim 10 further comprising a single open end for disposal of the medical device.

17. The container for dispensation, storage, transportation or disposal of a medical device comprising:
 a cylindrical section wherein the cylindrical section comprises a first open end and a second open end;
 a first collar assembly engaging the first open end and a second collar assembly engaging the second open end wherein the first collar assembly and the second collar assembly each have an access opening;
 a first locking mechanism engaging the first collar assembly and a second locking mechanism engaging the second collar assembly wherein the first locking mechanism and the second locking mechanism are capable of moving between a first unlocked position and a second locked position; and
 a first actuator engaging the first locking mechanism and a second actuator engaging the second locking mechanism wherein the first actuator is capable of controlling the movement of the first locking mechanism between the first unlocked position and the second locked position and the second actuator is capable of controlling the movement of the second locking mechanism between the first unlocked position and the second locked position.

18. The container of claim 17 wherein each of the first collar assembly and the second collar assembly comprises a first non-detachable segment proximal to the cylindrical section of the container and a second non-detachable segment distal to the cylindrical section of the container wherein the first non-detachable segment and the second non-detachable segment each have an access opening in communication with the cylindrical section of the container.

19. The container of claim 18 wherein the first locking mechanism is located between the first non-detachable segment proximal to the cylindrical section of the container and the second non-detachable segment distal to the cylindrical section of the container of the first collar assembly and the second locking assembly is located between the first non-detachable segment proximal to the cylindrical section of the container and the second non-detachable segment distal to the cylindrical section of the container of the second collar assembly.

20. The container of claim 18 wherein each of the first locking mechanism and the second locking mechanism comprise a rectangular plate having a slot capable of moving over a pin attached to the respective first non-detachable segment proximal to the cylindrical section, engaging a spring, the spring engaging the respective first non-detachable segment proximal to the cylindrical section and the spring capable of exerting a force enabling the pin to engage the rectangular plate, whereby movement of the rectangular plate causes the pin to be forced into the slot and causes the locking mechanism to lock.

21. The container of claim 17 wherein the first actuator extends externally from the first collar assembly and is capable of moving the first locking mechanism between the first unlocked position and the second locked position and the second actuator extends externally from the second collar assembly and is capable of moving the second locking mechanism between the first unlocked position and the second locked position.

22. The container of claim 17 wherein the cylindrical section is hollow.

* * * * *